US006994989B1

(12) United States Patent
Lyman

(10) Patent No.: US 6,994,989 B1
(45) Date of Patent: Feb. 7, 2006

(54) FLK-1 BINDING PROTEINS

(75) Inventor: Stewart D. Lyman, Seattle, WA (US)

(73) Assignee: Immunex Corp., Thousand Oaks, CA (US)

( * ) Notice: Subject to any disclaimer, the term of this patent is extended or adjusted under 35 U.S.C. 154(b) by 0 days.

(21) Appl. No.: 08/743,868

(22) Filed: Nov. 5, 1996

Related U.S. Application Data

(63) Continuation-in-part of application No. 08/554,374, filed on Nov. 8, 1995, now abandoned.

(51) Int. Cl.
C12N 15/12 (2006.01)
C12N 15/16 (2006.01)
C12N 16/63 (2006.01)
C12N 1/21 (2006.01)
C12N 5/10 (2006.01)

(52) U.S. Cl. .................. 435/69.1; 435/325; 435/243; 435/320.1; 536/23.5

(58) Field of Classification Search ............ 536/23.5; 435/320.1, 252.3, 325, 69.1, 243; 530/350
See application file for complete search history.

(56) References Cited

U.S. PATENT DOCUMENTS

| 5,185,438 A | 2/1993 | Lemischka ............ 536/23.2 |
| 5,283,354 A | 2/1994 | Lemischka ............ 536/23.5 |
| 5,607,918 A | 3/1997 | Eriksson et al. ........ 514/12 |
| 5,935,820 A * | 8/1999 | Hu et al. |
| 6,040,157 A * | 3/2000 | Hu et al. ............ 435/69.4 |
| 6,245,530 B1 * | 6/2001 | Alitalo et al. |
| 6,451,764 B1 * | 9/2002 | Lee et al. |

FOREIGN PATENT DOCUMENTS

| EP | 0 506 477 A1 | 9/1992 |
| WO | WO 92/14748 | 9/1992 |
| WO | WO 94/11499 | 5/1994 |
| WO | WO 95/21865 | 8/1995 |
| WO | WO 95/24473 | 9/1995 |
| WO | WO 96/26736 | 9/1996 |
| WO | WO 96/27007 | 9/1996 |
| WO | WO 96/39515 | 12/1996 |
| WO | WO 97/05250 | 2/1997 |
| WO | WO 97/09427 | 3/1997 |

OTHER PUBLICATIONS

Lee et al., "Vascular endothelial growth factor-related protein: A ligand and specific activator of the tyrosine kinase receptor Flt4", *Proc. Natl. Acad. Sci. USA* 93:1988-1992, 1996.

Joukov et al., "A Novel Vascular Endothelial Growth Factor, VEGF-C, is a Ligand for the Flt4 (VEGFR-3) and KDR (VEGFR-2) Receptor Tyrosine Kinases", *EMBO J.* 15:290-298, 1996.

Joukov et al., "A novel vascular endothelial growth factor, VEGF-C, is a ligand for the Flt4 (VEGFR-3)and KDR (VEGFR-2) receptor tyrosine kinases", *EMBO J.* 15:1751, 1996.

Printout of databank record for NCBI accession No. Z44272, Nov. 6, 1994.

Printout of databank record for accession No. X94216, Feb. 6, 1996.

Printout of databank record for accession No. U43142, Jan. 10, 1996.

Lyttle et al., "Homologs of Vascular Endothelial Growth Factor Are Encoded by the Poxvirus Orf Virus", *J. Virol.* 68:84-92, 1994.

Olofsson et al., "Vascular endothelial growth factor B, a novel growth factor for endothelial cells", *Proc. Natl. Acad. Sci. USA* 93:2576-2581, 1996.

Grimmond et al., "Cloning and Characterization of a Novel Human Gene Related to Vascular Endothelial Growth Factor", *Genome Research* 6:124-131, 1996.

Terman et al., "Identification of a new endothelial cell growth factor receptor tyrosine kinase", *Oncogene* 6:1677-1683, 1991.

Sarzani et al., "A Novel Endothelial Tyrosine Kinase cDNA Homologous to Platelet-Derived Growth Factor Receptor cDNA", *Biochem. Biophys. Res. Comm.* 186:706-714, 1992.

Matthews et al., "A receptor tyrosine kinase cDNA isolated from a population of enriched primitive hematopoietic cells and exhibiting close genetic linkage to *c-kit*", *Proc. Natl. Acad. Sci. USA* 88:9026-9030, 1991.

Terman et al., "Identification of the KDR tyrosine kinase as a receptor for vascular endothelial cell growth factor", *Biochem. Biophys. Res. Comm.* 187:1579-1586, 1992.

Millauer et al., "High Affinity VEGF Binding and Developmental Expression Suggest Flk-1 as a Major Regulator of Vasculogenesis and Angiogenesis", *Cell* 72:835-846, 1993.

Galland et al., "The *FLT4* gene encodes a transmembrane tyrosine kinase related to the vascular endothelial growth factor receptor", *Oncogene* 8:1233-1240, 1993.

Pajusola et al., "Two human FLT4 receptor tyrosine kinase isoforms with distinct carboxy terminal tails are produced by alternative processing of primary transcripts", *Oncogene* 8:2931-2937, 1993.

Pajusola et al., "Signalling properties of FLT4, a proteolytically processed receptor tyrosine kinase related to two VEGF receptors", *Oncogene* 9:3545-3555, 1994.

(Continued)

*Primary Examiner*—Christine J. Saoud

(74) *Attorney, Agent, or Firm*—Christine M. Bellas

(57) ABSTRACT

A protein designated flk-1bp binds the vascular endothelial cell surface receptor flk-1. Isolated DNA encoding flk-1bp is provided, along with expression vectors and transformed host cells useful in producing flk-1bp polypeptides. Antibodies that are immunoreactive with flk-1bp are generated using the polypeptides disclosed herein.

9 Claims, 1 Drawing Sheet

OTHER PUBLICATIONS

Kaipainen et al., "Expression of the fms-like tyrosine kinase 4 gene becomes restricted to lymphatic endothelium during development", *Proc. Natl. Acad. Sci. USA* 92:3566-3570, 1995.

Kaipainen et al., "Expression of the fms-like tyrosine kinase 4 gene becomes restricted to lymphatic endothelium during development", *Proc. Natl. Acad. Sci. USA* 92:3566-3570, 1995.

Mustonen and Alitalo, "Endothelial Receptor Tyrosine Kinases Involved in Angiogenesis", *J. Cell Biol.* 129:895-898, 1995.

De Vries et al., "The *fms*-Like Tyrosine Kinase, a Receptor for Vascular Endothelial Growth Factor", *Science* 255:989-991, 1992.

Yamaguchi et al., "flk-1, an flt-related receptor tyrosine kinase is an early marker for endothelial cell precursors", *Development* 118:489-498, 1993.

Ferrara et al., "The Vascular Endothelial Growth Factor Family of Polypeptides," *J. Cellular Biochemistry* 47:211-218, 1991.

Printout of databank record for accession No. N42368, Jan. 25, 1996.

Printout of databank record for accession No. N42374, Jan. 25, 1996.

* cited by examiner

FIGURE 1

```
Hu VEGF     mnfllswvhwsla   lllylhhakwsgaapmaegggqnhhevvkfmdv------------------
Hu PLGF     mpvmrlfpcflql   laglalpavppqqwalsagngssevevvpfqev------------------
Hu flk-1bp  mhllgffsvacsl   laaallpggpreapaaaaafesgldlsdaepdageatayaskdleeql Hu VEGF     ------------------------------------------------------------
Hu PLGF     ------------------------------------------------------------
Hu flk-1bp  rsvssvdelmtvlypeywkmykcqlrkggwqhnreqanlnsrteetikfaaahynteilk Hu VEGF     -----YQRSY CHPI ETLV DIFQ EYPDEIEYI FKPSCV PLM RGGCC ND EGLE CVPTEESN
Hu PLGF     -----WGRSY CRAL ERLV DVVS EYPSEVEHM FSPSCV SLL RCTGCC GD ENLH CVPVETAN
Hu flk-1bp  sidneWRKTQ CMPR EVCI DVGK EFGVATNTF EKEPCV SVY RCGGCC NS EGLQ CMNTSTSY Hu VEGF     ITMQIMR IKPH--QGQHIGEM CFLQHNK CECRPKKDRARQenpcqp---------------
Hu PLGF     VTMQLLK IRSGDRPSYVELTF SQHVRCE CRplrekmpkercgdavp Cr--------------
Hu flk-1bp  LSKTLFE ITVPLSQGPKPVTI SFANHTS CRCMSKLDVYRQvhsiir Eslpatlpqcqaan Hu VEGF     ------------------------------------------------------------
Hu PLGF     ------------------------------------------------------------
Hu flk-1bp  ktcptnymwnnhicrcDagedfmfssdagddstdgfhdicgpnkeldeetcqcvcraglr Hu VEGF     ----------------------------------- CSERRKHLFVQD EQT CKC
Hu PLGF     ----------------------------------- CKRTCPRNQPLN EGK CAC
Hu flk-1bp  pascgphkeldrnscgcvcknklfpsqcganrefdentcqcv Hu VEGF     SCKNTDSRCKARQELELNER     TCRCDKPRR---------------------------
Hu PLGF     ----------------------------------------------------------
Hu flk-1bp  ECTESPQKCLLKGKKFHHQ      TCSCyrrpctnrqkacepgfsyseevcrcvpsywkrpqms
```

FLK-1 BINDING PROTEINS

This application is a continuation-in-part of application Ser. No. 08/554,374, filed Nov. 8, 1995, now abandoned.

BACKGROUND OF THE INVENTION

The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). Several receptor tyrosine kinases, and growth factors that bind thereto, have been suggested to play a role in angiogenesis, although some may promote angiogenesis indirectly (Mustonen and Alitalo, *J. Cell Biol.* 129: 895–898, 1995).

One such receptor tyrosine kinase, known as fetal liver kinase 1 (flk-1), is a member of the type III subclass of RTKs. An alternative designation for human flk-1 is kinase insert domain-containing receptor (KDR) (Terman et al., *Oncogene* 6:1677–83, 1991), and the rat homolog has been termed TKr-C (Sarzani et al., *Biochem. Biophys. Res. Comm.* 186:706–714, 1992). DNAs encoding mouse, rat and human flk-1 have been isolated, and the nucleotide and encoded amino acid sequences reported (Matthews et al., *Proc. Natl. Acad. Sci. USA,* 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993).

The type III subclass RTK designated fms-like tyrosine kinase-1 (flt-1) is related to flk-1 (DeVries et al., *Science* 255:989–991, 1992; Shibuya et al., *Oncogene* 5:519–524, 1990). Flt-1 is believed to be essential for endothelial organization during vascular development. Flt-1 expression is associated with early vascular development in mouse embryos, and with neovascularization during wound healing (Mustonen and Alitalo, supra). Expression of flt-1 in adult organs suggests an additional function for this receptor that is not related to cell growth (Mustonen and Alitalo, supra).

Another RTK that is related to flt1 and flk1 is flt4 (Galland et al., *Oncogene* 8:1233–40, 1993; Pajusola et al., *Oncogene* 8:2931–37, 1993). Features shared by these three receptors include the seven immunoglobulin-like domains in their extracellular region. The amino acid sequence of flt4 exhibits significant homology with the sequences of flt1 and flk-1, especially in the tyrosine kinase domain (Galland et al., supra). Unlike flt-1 and flk-1, however, a precursor form of flt-4 is cleaved during post-translational processing to form two disulfide-linked polypeptides (Pajusola et al., supra). Studies of Flt-4 expression during development support the theory of venous origin of lymphatic vessels (Kaipainen et al., *Proc. Natl. Acad. Sci. USA* 92:3566–70, April, 1995).

Given the crucial role of endothelial cells in angiogenesis, growth factors that act on endothelial cells are of particular interest for studies of the regulation of vascularization. One such factor is vascular endothelial cell growth factor (VEGF), which binds to both flk-1 and flt-1 with relatively high affinity and is mitogenic toward vascular endothelial cells (Terman et al., 1992, supra; Mustonen et al. supra; DeVries et al., supra). VEGF does not bind to flt4 (Pajusola et al., supra). The studies reported in Millauer et al., supra, suggest that VEGF and flk-1 are a ligand-receptor pair that play an important role in the formation and sprouting of blood vessels, termed vasculogenesis and angiogenesis, respectively.

Different forms of VEGF arising from alternative splicing of mRNA have been reported, including the four species described by Ferrara et al. (*J. Cell. Biochem.* 47:211–218, 1991). Both secreted and predominantly cell-associated species of VEGF were identified by Ferrara et al. supra, and the protein is known to exist in the form of disulfide linked dimers.

Placenta growth factor (PlGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PlGF arise from alternative splicing of mRNA, and the protein exists in dimeric form (Park et al., supra). PlGF binds flt-1 with high affinity, but not flk-1 (Park et al., supra). PlGF potentiates the mitogenic effect of VEGF on endothelial cells when VEGF is present at low concentrations, but has no detectable effect when VEGF is present at higher concentrations (Park et al., supra.).

Studies of growth factors and receptors that are believed to regulate angiogenesis include those discussed above. Investigation into the existence and identity of other such receptors, and proteins that bind thereto, is desirable. Identifying such proteins would provide additional means for elucidating the effects of various ligand-receptor signaling systems on development and differentiation of the vascular system, as well as providing further insight into, and means for, regulation of such biological processes.

Inhibiting angiogenesis is desirable in certain clinical situations (e.g., to suppress growth and mestastasis of solid tumors, or in treating rheumatoid arthritis), whereas promoting vascularization is beneficial for treating other conditions (e.g., wound healing). Consequently, molecules that promote angiogenesis by transducing signals through the above-discussed receptors, and molecules capable of inhibiting such signal transduction, are both of interest.

SUMMARY OF THE INVENTION

The present invention provides a novel protein designated flk-1 binding protein (flk-1bp), as well as isolated DNA encoding the novel protein and expression vectors comprising the isolated DNA. A method for producing flk-1bp involves culturing host cells transformed with the recombinant expression vectors under conditions appropriate for expression of flk-1bp, then recovering the protein from the culture. Secreted flk-1bp polypeptides are recovered from the culture medium.

The flk-1bp protein is able to bind to a cell surface receptor known as human flk-1 or KDR. This receptor is expressed on cell types that include vascular endothelial cells. Antibodies that specifically bind flk-1bp polypeptides are also provided.

BRIEF DESCRIPTION OF THE DRAWINGS

FIG. 1 presents an alignment of the amino acid sequences of three proteins, which are a human flk-1 binding protein of the present invention (flk-1bp) (SEQ ID NO:2), a human vascular endothelial cell growth factor (VEGF) (SEQ ID NO:4), and a human placenta growth factor (PLGF) (SEQ ID NO:5). Gaps were introduced as necessary to maximize the alignment. Residues found in at least two of the sequences are boxed.

DETAILED DESCRIPTION OF THE INVENTION

A novel protein designated Flk-1bp is provided herein, along with DNA encoding flk-1bp and recombinant expression vectors comprising the flk-1bp DNA. A method for producing recombinant flk-1bp polypeptides involves cultivating host cells transformed with the expression vectors under conditions appropriate for expression of flk-1bp, and recovering the expressed flk-1bp.

The present invention also provides antibodies that specifically bind flk-1bp proteins. In one embodiment, the antibodies are monoclonal antibodies.

Isolation of a DNA encoding a human flk-1bp is described in example 1 below. The nucleotide sequence of the human flk-1bp DNA isolated in example 1 is presented in SEQ ID NO:1, and the amino acid sequence encoded thereby is presented in SEQ ID NO:2. This human flk-1bp is a secreted protein that comprises an N-terminal signal peptide (amino acids −20 through, −1 of SEQ ID NO:2) when initially synthesized. The signal peptide is cleaved during secretion of the protein from the cell, yielding a mature protein comprising amino acids 1 to 399 of SEQ ID NO:2.

E. coli strain DH10B cells transformed with a recombinant vector containing this human flk-1bp DNA were deposited with the American Type Culture Collection on Sep. 1, 1995, and assigned accession no. ATCC 69897. The deposit was made under the terms of the Budapest Treaty. As described in more detail in example 1, the recombinant vector in the deposited strain contains human flk-1bp DNA that includes the entire coding region shown in SEQ ID NO:1.

In one embodiment, the present invention provides a flk-1bp protein encoded by the flk-1bp DNA insert of the vector in deposited strain ATCC 69897. flk-1bp protein expressed by a host cell transformed with an expression vector containing the flk-1bp DNA insert found in the vector in strain ATCC 69897 is provided.

The flk-1bp of SEQ ID NO:2 contains an N-terminal signal peptide, and is capable of being secreted from suitable host cells in which it is expressed. The flk-1bp thus may be recovered from the culture medium, which facilitates purification.

Vascular endothelial cell growth factor (VEGF) binds to the receptor tyrosine kinase flk-1 (DeVries et al. supra). As demonstrated in example 3, human flk-1bp demonstrated the ability to compete with VEGF for binding to human flk-1.

FIG. 1 presents an alignment of the amino acid sequences of three proteins, which are a human flk-1 binding protein of the present invention (flk-1bp) (SEQ ID NO:2), a human vascular endothelial cell growth factor (VEGF) (SEQ ID NO:4), and a human placenta growth factor (PLGF) (SEQ ID NO:5). Gaps were introduced as necessary to maximize the alignment. Residues found in at least two of the sequences are boxed.

As described in example 1, a search of a sequence databank was performed, using a human VEGF amino acid sequence as the query sequence. An expressed sequence tag (EST) file, GenBank accession number Z44272, was identified by the search. The 299-nucleotide sequence presented in file no. Z44272 corresponds to nucleotides 660 to 958 of SEQ ID NO:1, with the exception of nucleotide number 733, which was not identified in file no. Z44272. The NCBI/GenBank record does not disclose any polypeptide encoded by the EST of file no. Z44272, and does not indicate what the reading frame, if any, might be.

One embodiment of the present invention is directed to mature human flk-1bp protein characterized by the N-terminal amino acid sequence Gly-Pro-Arg-Glu-Ala-Pro-Ala-Ala-Ala-Ala-Ala-Phe-Glu-Ser-Gly-(amino acids 1–15 of SEQ ID NO:2). As described in example 1, the present invention provides mature flk-1bp protein characterized by a calculated molecular weight of 44,823 daltons and an isoelectric point of 8.678.

The flk-1bp polypeptides of the present invention include polypeptides having amino acid sequences that differ from, but are highly homologous to, that presented in SEQ ID NO:2. Examples include, but are not limited to, homologs derived from other mammalian species (which can be identified by cross-species hybridization using human flk-1bp DNA as a probe), variants (both naturally occurring variants and those generated by recombinant DNA technology), and flk-1bp fragments that retain a desired biological activity. Such polypeptides exhibit a biological activity of the flk-1bp proteins of SEQ ID NO:2, and preferably comprise an amino acid sequence that is at least 80% identical (most preferably at least 90% identical) to the amino acid sequence presented in SEQ ID NO:2. These embodiments of the present invention are described in more detail below.

flk-1bp fragments may be prepared by any of a number of conventional techniques. A DNA sequence encoding a desired flk-1bp fragment may be subcloned into an expression vector for production of the flk-1bp fragment. The desired flk-1bp-encoding DNA fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5′ or 3′ terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well known polymerase chain reaction (PCR) procedure also may be employed to isolate and amplify a DNA sequence encoding a desired protein fragment. Oligonucleotides that define the desired termini of the DNA fragment are employed as 5′ and 3′ primers. The oligonucleotides may additionally contain recognition sites for restriction endonucleases, to faciliate insertion of the amplified DNA fragment into an expression vector. PCR techniques are described in Saiki et al., Science 239:487 (1988); Recombinant DNA Methodology, Wu et al., eds., Academic Press, Inc., San Diego (1989), pp. 189–196; and PCR Protocols: A Guide to Methods and Applications, Innis et al., eds., Academic Press, Inc. (1990).

The flk-1bp signal peptide discussed above is identified in accordance with conventional criteria for identifying that type of hydrophobic domain. Computer programs that predict the site of cleavage of a signal peptide are available. However, more than one possible cleavage site may be identified by such computer programs, and it is recognized in the pertinent field that cleavage can occur at sites other than those predicted. Signal peptide cleavage sites that are less likely, but possible, for flk-1bp occur after residue −6 (in which case the mature protein contains amino acids −5 to 399 of SEQ ID NO:2) or after residue −5 (in which case the mature protein contains amino acids −4 to 399 of SEQ ID NO:2). As will be understood by the skilled artisan, a protein preparation can comprise a mixture of protein molecules having different N-terminal amino acids, due to cleavage of the signal peptide at more than one site.

In addition, post-translational processing can vary according to the particular expression system employed. Consequently, the N- or C-terminal amino acid of a recombinant protein may vary according to the type of host cells in which the protein was expressed, for example. Particular embodiments include but are not limited to flk-1bp proteins having an N-terminal amino acid selected from any of amino acids −5, −4, −3, −2, −1, 1, 2, 3, 4, and 5; and a C-terminal amino acid selected from amino acids 395 to 399 of SEQ ID NO:2.

Mature flk-1bp provided herein includes such naturally occuring variants, in which the N-terminal amino acid is other than the residue at position 1, or the C-terminal amino acid is other than amino acid 399, of SEQ ID NO:2. Other naturally occurring flk-1bp variants encompassed by the present invention are those arising from alternative mRNA splicing events (since flk-1bp is encoded by a multi-exon gene). Other naturally occurring variants are allelic variants.

The flk-1bp DNA of the present invention includes cDNA, chemically synthesized DNA, DNA isolated by PCR, genomic DNA, and combinations thereof. Genomic flk-1bp DNA may be isolated by hybridization to the flk-1bp cDNA disclosed herein using standard techniques. RNA transcribed from the flk-1bp DNA is also encompassed by the present invention.

Certain embodiments of the present invention provide isolated DNA comprising a nucleotide sequence selected from the group consisting of nucleotides 188 to 1444 of SEQ ID NO:1 (human flk-1bp coding region) and nucleotides 248 to 1444 of SEQ ID NO:1 (encoding a mature human flk-1bp protein). DNAs encoding biologically active fragments of the protein of SEQ ID NO:2 are also provided.

Due to degeneracy of the genetic code, two DNA sequences may differ, yet encode the same amino acid sequence. The present invention thus provides isolated DNA sequences encoding biologically active flk-1bp, selected from DNA comprising the coding region of a native flk-1bp cDNA, or fragments thereof, and DNA which is degenerate as a result of the genetic code to a native flk-1bp-encoding DNA sequence.

Also provided herein are purified flk-1bp polypeptides, both recombinant and non-recombinant. Variants and derivatives of native flk-1bp proteins that retain a desired biological activity are also within the scope of the present invention. In one embodiment, the biological activity of a flk-1bp variant is essentially equivalent to a desired biological activity of a native flk-1bp protein. One biological activity of human flk-1bp is the ability to bind human flk-1. The ability of a flk-1bp polypeptide (including variants thereof) to bind flk-1 can be determined in a conventional binding assay.

It is possible that flk-1bp can bind to other receptors that are related to flk-1, such as flt-1. The ability of flk-1bp to bind to flt-1 can be determined in binding assays. As an alternative to binding assays, assays for a biological effect resulting from interaction of flk-1bp with a given receptor may be employed. Examples include signal transduction assays. Phosphorylation of a receptor upon binding flk-1bp may be detected by known procedures, which may include use of commercially available anti-phosphotyrosine antibodies (Chemicon International, Temecula, Calif.). Additional receptors with which flk-1bp interacts thus may be identified.

A receptor tyrosine kinase designated flt-4 has been described (Galland et al., *Oncogene* 8:1233–40, 1993; Pajusola et al., *Oncogene* 8:2931–37, 1993; Kaipainen et al., *Proc. Natl. Acad. Sci. USA* 92:3566–70, April, 1995). The flk-1bp of the present invention binds, and induces phosphorylation of, flt-4.

flk-1bp variants may be obtained by mutations of native flk-1bp nucleotide sequences, for example. An flk-1bp variant, as referred to herein, is a polypeptide substantially homologous to a native flk-1bp, but which has an amino acid sequence different from that of native flk-1bp because of one or a plurality of deletions, insertions or substitutions. flk-1bp-encoding DNA sequences of the present invention encompass sequences that comprise one or more additions, deletions, or substitutions of nucleotides when compared to a native flk-1bp DNA sequence, but that encode an flk-1bp protein that is essentially biologically equivalent to a native flk-1bp protein.

The variant amino acid or DNA sequence preferably is at least 80% identical to a native flk-1bp sequence, most preferably at least 90% identical. In particular embodiments, DNA or amino acid sequences are at least 95%, 96%, 97%, 98%, or 99% identical to the sequence presented in SEQ ID NOS:1 or 2. The degree of homology (percent identity) between a native and a mutant sequence may be determined, for example, by comparing the two sequences using computer programs commonly employed for this purpose. One suitable program is the GAP computer program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Briefly, the GAP program defines identity as the number of aligned symbols (i.e., nucleotides or amino acids) which are identical, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

DNA sequences encoding flk-1bp (including fragments and variants thereof) include DNA sequences that will hybridize to a native flk-1bp DNA under conditions of moderate or severe stringency, wherein the encoded flk-1bp retains a desired biological activity (e.g., the ability to bind flk-1). Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press (1989). Conditions of moderate stringency, as defined by Sambrook et al., include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing, as is understood by one skilled in the field of molecular biology. In one embodiment of the invention, a flk-1bp is encoded by a DNA sequence that will hybridize under severely stringent conditions to a DNA sequence comprising nucleotides 188 to 1444 of SEQ ID NO:1 (the coding region of the flk-1bp DNA of SEQ ID NO:1). The severely stringent conditions include hybridization at 68° C. followed by washing in 0.1×SSC/0.1% SDS at 63–68° C. flk-1bp polypeptides encoded by such hybridizing DNA sequences are provided herein.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Techniques for making such alterations include those disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering: Principles and Methods*, Plenum Press, 1981); and U.S. Pat. Nos. 4,518,584 and 4,737,462, which are incorporated by reference herein.

Variants may comprise conservatively substituted sequences, meaning that one or more amino acid residues of a native flk-1bp polypeptide are replaced by different residues, but that the conservatively substituted flk-1bp polypeptide retains a desired biological activity that is essentially equivalent to that of a native flk-1bp polypeptide. Examples of conservative substitutions include substitution of amino acids that do not alter the secondary and/or tertiary structure of flk-1bp. Other examples involve substitution of amino acids outside of the receptor-binding domain, when the desired biological activity is the ability to bind to a particular receptor.

A given amino acid may be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. flk-1bp polypeptides comprising conservative amino acid substitutions may be tested in one of the assays described herein to confirm that a desired biological activity of a native flk-1bp is retained. DNA sequences encoding flk-1bp polypeptides that contain such conservative amino acid substitutions are encompassed by the present invention.

Residues in flk-1bp that are conserved, in that identical residues in VEGF or PlGF (or both) are aligned with these flk-1bp residues in FIG. 1, are amino acids −20, −7, 111, 115, 119, 123, 132, 134, 136, 137, 141, 142, 144–146, 149, 151, 153, 168, 182, 189, 207, 323, 335, 338, 340, 342, 360, 361, and 363 of SEQ ID NO:2. Advantageously, these conserved amino acids are not altered when generating conservatively substituted sequences or other variants of a native flk-1bp.

The conserved amino acids in mature flk-1bp are clustered into two regions, namely, from amino acids 111 to 207, and from amino acids 323 to 363 of SEQ ID NO:2. flk-1bp fragments that contain the conserved amino acids are encompassed by the present invention. Such fragments may contain amino acids 111 to 207 of SEQ ID NO:2, or amino acids 323 to 363 of SEQ ID NO:2, or both.

FIG. 1 shows that there are no sequences in VEGF or PlGF that are aligned with amino acids 27 through 105, amino acids 209 through 322, and amino acids 369 through 399 of SEQ ID NO:2. Fragments of flk-1bp that lack from one to all of residues 27 through 105, 209 through 322, or 369 through 399 of SEQ ID NO:2 are encompassed by the present invention.

VEGF binds flk-1 and flt-1, whereas PlGF binds flt-1 but not flk-1. It is noteworthy that PlGF contains the conserved amino acids that are clustered in the region aligned with amino acids 111 to 207 of flk-1bp, but lacks the conserved amino acids found between amino acids 323 to 363 of flk-1bp. VEGF contains both groups of conserved amino acids.

flk-1bp may be modified to create flk-1bp derivatives by forming covalent or aggregative conjugates with other chemical moieties, such as glycosyl groups, lipids, phosphate, acetyl groups and the like. Covalent derivatives of flk-1bp may be prepared by linking the chemical moieties to functional groups on flk-1bp amino acid side chains or at the N-terminus or C-terminus of a flk-1bp polypeptide or the extracellular domain thereof.

Other derivatives of flk-1bp within the scope of this invention include covalent or aggregative conjugates of flk-1bp or its fragments with other proteins or polypeptides, such as by synthesis in recombinant culture as N-terminal or C-terminal fusions. For example, the conjugate may comprise a heterologous signal or leader polypeptide sequence in place of the native signal peptide at the N-terminus of a flk-1bp polypeptide. The signal or leader peptide co-translationally or post-translationally directs transfer of the conjugate from its site of synthesis to a site inside or outside of the cell membrane or cell wall. Another example is a fusion protein comprising flk-1bp and a polypeptide that promotes oligomerization. Examples of such fusion proteins are described in more detail below.

flk-1bp polypeptide fusions can comprise peptides added to facilitate purification and identification of flk-1bp. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:3), which is highly antigenic and provides an epitope reversibly bound by a specific monoclonal antibody, thus enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A murine hybridoma designated 4E11 produces a monoclonal antibody that binds the peptide DYKDDDDK (SEQ ID NO:3) in the presence of certain divalent metal cations (as described in U.S. Pat. No. 5,011,912), and has been deposited with the American Type Culture Collection under accession no HB 9259. Expression systems useful for producing recombinant proteins fused to the FLAG® peptide, as well as monoclonal antibodies that bind the octapeptide and are useful in purifying the recombinant proteins, are available from Eastman Kodak Company, Scientific Imaging Systems, New Haven, Conn. In one embodiment, the FLAG® peptide is fused to the C-terminal end of a flk-1bp polypeptide.

The present invention further includes flk-1bp polypeptides with or without associated native-pattern glycosylation. flk-1bp expressed in yeast or mammalian expression systems may be similar to or significantly different from a native flk-1bp polypeptide in molecular weight and glycosylation pattern, depending upon the choice of expression system. Expression of flk-1bp polypeptides in bacterial expression systems, such as *E. coli*, provides non-glycosylated molecules.

Glycosylation sites in the flk-1bp extracellular domain can be modified to preclude glycosylation while allowing expression of a homogeneous, reduced carbohydrate analog using yeast or mammalian expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain. Known procedures for inactivating N-glycosylation sites in proteins include those described in U.S. Pat. No. 5,071,972 and EP 276,846. Three potential N-glycosylation sites are found in SEQ ID NO:2, at positions 155–157, 185–187, and 220–222.

In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. Potential KEX2 protease processing sites are found at positions 66–67, 107–108, 206–207, 324–325, 365–366, and 395—395 in SEQ ID NO:2.

flk-1bp polypeptides of the present invention, which include fragments, variants, and derivatives of native flk-1bp proteins, may be tested for the ability to bind a particular receptor using conventional assay techniques. Procedures for conducting binding assays, including competition binding assays, are well known.

A flk-1bp may be labeled with a detectable reagent (e.g., radioiodinated). Cells expressing flk-1 are contacted with the labeled flk-1bp, then washed to remove unbound reagents. Cell-associated radioactivity indicates binding of flk-1bp to the cells.

As illustrated in example 2, a flk-1bp may be tested for the ability to compete with VEGF for binding to flk-1 (i.e., a competitive binding assay). Likewise, biological activity of a flk-1bp variant, derivative, or fragment may be assessed by assaying for the variant's ability to compete with VEGF, or with a native flk-1bp, for binding to flk-1.

Reagents that may be employed in competitive binding assays include radiolabeled flk-1bp and intact flk-1-expressing cells. For example, radiolabeled native flk-1bp can be used to compete with a flk-1bp variant for binding to cell surface flk-1. Instead of intact cells, one could substitute a soluble flk-1/Fc fusion protein bound to a solid phase through the interaction of Protein A or Protein G with the Fc moiety. Chromatography columns that contain Protein A and Protein G include those available from Pharmacia Biotech, Inc., Piscataway, N.J. Another type of competitive binding assay utilizes radiolabeled soluble flk-1 and immobilized flk-1bp (e.g., an immobilized flk-1bp/Fc fusion protein). Qualitative results can be obtained by competitive autoradiographic plate binding assays, or Scatchard plots may be utilized to generate quantitative results. Affinity calculations (Scatchard, Ann. N.Y. Acad. Sci. 51:660, 1949) may be generated on RS/1 (BBN Software, Boston, Mass.) run on a Microvax computer.

As another alternative, binding may be detected by using a biosensor unit. One example of such a procedure involves immobilizing a flk-1/Fc fusion protein on the chip of a biosensor unit, as follows. Goat anti-human IgG directed against the Fc region (Jackson Immunoresearch Laboratories, Inc., West Grove, Pa.) was chemically bound to the chip of a BIAcore Processing Unit (Pharmacia Biosensor) by standard techniques. A flk-1/Fc protein was then bound to the immobilized goat anti-human IgG via interaction of the antibody with the Fc moiety of the fusion protein. Culture medium from cells expressing a flk-1bp then is allowed to flow across the chip. Binding of a protein to the immobilized flk-1/Fc is indicated by a significant resonance shift on the Biosensor. The presence of a protein that binds flk-1bp in the culture medium is thus confirmed.

Oligomers

The present invention encompasses flk-1bp polypeptides in the form of oligomers, such as dimers, trimers, or higher oligomers. Oligomers may be formed by disulfide bonds between cysteine residues on different flk-1bp polypeptides, or by non-covalent interactions between flk-1bp polypeptide chains, for example. In other embodiments, oligomers comprise from two to four flk-1bp polypeptides joined via covalent or non-covalent interactions between peptide moieties fused to the flk-1bp polypeptides. Such peptides may be peptide linkers (spacers), or peptides that have the property of promoting oligomerization. Leucine zippers and certain polypeptides derived from antibodies are among the peptides that can promote oligomerization of flk-1bp polypeptides attached thereto, as described in more detail below.

Preparation of fusion proteins comprising heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:667, 1990); and Hollenbaugh and Aruffo ("Construction of Immunoglobulin Fusion Proteins", in *Current Protocols in Immunology, Supplement* 4, pages 10.19.1–10.19.11, 1992), hereby incorporated by reference. In one embodiment of the invention, a flk-1bp dimer is created by fusing flk-1bp to an Fc region polypeptide derived from an antibody. The term "Fc polypeptide" includes native and mutein forms, as well as truncated Fc polypeptides containing the hinge region that promotes dimerization.

A gene fusion encoding the flk-1bp/Fc fusion protein is inserted into an appropriate expression vector. The flk-1bp/Fc fusion proteins are allowed to assemble much like antibody molecules, whereupon interchain disulfide bonds form between the Fc polypeptides, yielding divalent flk-1bp. In other embodiments, flk-1bp may be substituted for the variable portion of an antibody heavy or light chain. If fusion proteins are made with both heavy and light chains of an antibody, it is possible to form an flk-1bp oligomer with as many as four flk-1bp polypeptides.

One suitable Fc polypeptide is the native Fc region polypeptide derived from a human IgG1, which is described in PCT application WO 93/10151, hereby incorporated by reference. Another useful Fc polypeptide is the Fc mutein described in U.S. Pat. No. 5,457,035 and in Baum et al., *EMBO J.* 13:3992, 1994. The amino acid sequence of the mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

Alternatively, oligomeric flk-1bp may comprise two or more flk-1bp polypeptides joined through peptide linkers. Examples include those peptide linkers described in U.S.

Pat. No. 5,073,627 (hereby incorporated by reference). Fusion proteins comprising multiple flk-1bp polypeptides separated by peptide linkers may be produced using conventional recombinant DNA technology.

Another method for preparing oligomeric flk-1bp polypeptides involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize. Examples of leucine zipper domains suitable for producing oligomeric flk-1bp proteins are those described in PCT application WO 94/10308, hereby incorporated by reference. Recombinant fusion proteins comprising a flk-1bp polypeptide fused to a peptide that dimerizes or trimerizes in solution are expressed in suitable host cells, and the resulting oligomeric flk-1bp is recovered from the culture supernatant.

In one embodiment, a leucine zipper moiety that preferentially forms trimers is employed. One example is a leucine zipper derived from lung surfactant protein D (SPD), as described in Hoppe et al. (*FEBS Letters* 344:191, 1994). Other peptides derived from naturally occurring trimeric proteins may be employed in preparing trimeric flk-1bp.

Expression Systems

The present invention provides recombinant expression vectors for expression of flk-1bp, and host cells transformed with the expression vectors. Any suitable expression system may be employed. The vectors include a DNA encoding a flk-1bp polypeptide, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the flk-1bp DNA sequence. Thus, a promoter nucleotide sequence is operably linked to an flk-1bp DNA sequence if the promoter nucleotide sequence controls the transcription of the flk-1bp DNA sequence. An origin of replication that confers the ability to replicate in the desired host cells, and a selection gene by which transformants are identified, are generally incorporated into the expression vector.

Advantageously, a sequence encoding an appropriate signal peptide, either native or heterologous, is incorporated into the expression vectors. A DNA sequence for a signal peptide (secretory leader) may be fused in frame to the flk-1bp sequence so that the flk-1bp is initially translated as a fusion protein comprising the signal peptide. A signal peptide that is functional in the intended host cells promotes extracellular secretion of the flk-1bp polypeptide. The signal peptide is cleaved from the flk-1bp polypeptide upon secretion of flk-1bp from the cell. Heterologous signal or leader peptides may be employed when such peptides promote secretion of higher levels of flk-1bp from the particular host cells employed.

Suitable host cells for expression of flk-1bp polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce flk-1bp polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a flk-1bp polypeptide may include an N-terminal methionine residue to facilitate expression of the recombinant polypeptide in the prokaryotic host cell. The N-terminal Met may be cleaved from the expressed recombinant flk-1bp polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a flk-1bp DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9, ATCC 37092) and pPLc28 (resident in *E. coli* RR1, ATCC 53082).

flk-1bp alternatively may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene.

Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the flk-1bp polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Mammalian or insect host cell culture systems could also be employed to express recombinant flk-1bp polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CVI/EBNA cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983), for example. A useful system for stable high level expression of mammalian cDNAs in C127 murine mammary epithelial cells can be constructed substantially as described by Cosman et al. (*Mol. Immunol.* 23:935, 1986). A high expression vector, PMLSV N1/N4, described by Cosman et al., *Nature* 312:768, 1984 has been deposited as ATCC 39890. Additional examples of mammalian expression vectors are described in EP-A-0367566, and in WO 91/18982. The vectors may be derived from retroviruses.

If desired, a heterologous signal or leader peptide may be substituted for the native flk-1bp signal peptide. Signal or leader peptides are chosen according to the particular host cell that is to be employed.

Examples of alternative signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. Synthetic signal peptides, which are not naturally occurring but can be generated through recombinant DNA technology, are yet another alternative.

Purified flk-1bp Protein

The present invention provides purified flk-1bp proteins, which may be produced by recombinant expression systems as described above or purified from naturally occurring cells. The desired degree of purity may depend on the intended use of the protein. A relatively high degree of purity is desired when the protein is to be administered in vivo, for example. Advantageously, flk-1bp polypeptides are purified such that no protein bands corresponding to other proteins are detectable by SDS-polyacrylamide gel electrophoresis (SDS-PAGE). It will be recognized by one skilled in the pertinent field that multiple bands corresponding to flk-1bp protein may be detected by SDS-PAGE, due to differential glycosylation, variations in post-translational processing, and the like, as discussed above. A preparation of flk-1bp protein is considered to be purified as long as no bands corresponding to different (non-flk-1bp) proteins are visualized. flk-1bp most preferably is purified to substantial homogeneity, as indicated by a single protein band upon analysis by SDS-PAGE. The protein band may be visualized by silver staining, Coomassie blue staining, or (if the protein is radiolabeled) by autoradiography.

One process for producing the flk-1bp protein comprises culturing a host cell transformed with an expression vector comprising a DNA sequence that encodes flk-1bp under conditions such that flk-1bp is expressed. The flk-1bp protein is then recovered from the culture medium. As the skilled artisan will recognize, procedures for purifying the recombinant flk-1bp will vary according to such factors as the type of host cells employed.

For example, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify flk-1bp. Some or all of the foregoing purification steps, in various combinations, can be employed to provide a purified flk-1bp protein.

Recombinant protein produced in bacterial culture may be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells may be employed to express flk-1bp, preferably as a secreted polypeptide to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Alternatively, flk-1bp polypeptides can be purified by immunoaffinity chromatography. An affinity column containing an immobilized antibody that binds flk-1bp may be prepared by conventional procedures and employed in purifying flk-1bp. Example 3 describes a procedure for generating monoclonal antibodies directed against flk-1bp.

Properties and Uses of flk-1bp

The flk-1bp of the present invention binds to the receptor known as human flk-1 or KDR (Terman et al., *Oncogene* 6:1677–83, 1991; Terman et al., *Biochem. Biophys. Res. Comm.* 187:1579–86, 1992). As demonstrated in example 2, human flk-1bp competes with VEGF for binding to human flk-1. A number of uses flow from this property of flk-1bp.

flk-1 is expressed on vascular endothelial cells. flk-1bp polypeptides may be used to purify vascular endothelial cells, or any cell type to which flk-1bp binds. In one embodiment, the cells are purified by affinity chromatography, using a chromatography matrix having flk-1bp bound thereto. The flk-1bp attached to the chromatography matrix may be a full length protein, a flk-1bp fragment, a flk-1bp-containing fusion protein, or other suitable flk-1bp polypeptide described herein. In one embodiment, a flk-1bp/Fc fusion protein is bound to a Protein A or Protein G column through interaction of the Fc moiety with the Protein A or Protein G. Alternatively, flk-1bp may be used in isolating vascular endothelial cells by flow cytometry.

The flk-1bp also finds use as a protein purification reagent. Human flk-1 may be purified by affinity chromatography, for example, using a chromatography matrix having flk-1bp bound thereto.

Preparations of vascular endothelial cells and flk-1 are useful to those studying the roles of such cells and receptor tyrosine kinases in vasculogenesis and angiogenesis (formation and sprouting of blood vessels, respectively) (Millauer et al., supra, and Mustonen et al., supra). The disclosure herein of the flk-1bp of the present invention allows investigation of the role that this novel protein may play in vasculogenesis or angiogenesis.

Angiogenesis is essential for a number of normal processes (such as embryonic development, somatic growth, cyclical growth of endometrium, and wound healing), yet has been implicated in certain pathological conditions as well (e.g., rheumatoid arthritis and the growth and mestastasis of solid tumors). See Ferrara et al. (*J. Cell. Biochem.* 47:211, 1991; and Folkman, J. (*Nature Med.*, 1:27–31, 1995), hereby incorporated by reference.

The flk-1bp of the present invention may be used in developing treatments for any disorder mediated (directly or indirectly) by defective or insufficient amounts of flk-1bp. A therapeutically effective amount of purified flk-1bp protein is administered to a patient afflicted with such a disorder. Alternatively, flk-1bp DNA sequences may be employed in developing a gene therapy approach to treating such disorders. Disclosure herein of native flk-1bp nucleotide sequences permits the detection of defective flk-1bp genes, and the replacement thereof with normal flk-1bp-encoding genes. Defective genes may be detected in in vitro diagnostic assays, and by comparision of the native flk-1bp nucleotide sequence disclosed herein with that of an flk-1bp gene derived from a person suspected of harboring a defect in this gene.

Polypeptides of the present invention also may be employed as carriers, for delivering diagnostic or therapeutic agents to any cells to which flk-1bp binds. As discussed above, such cells include but are not limited to cells bearing flk-1. Flk-1bp can be used to deliver diagnostic or therapeutic agents to these cells in in vitro or in vivo procedures. Such cells are contacted with a conjugate comprising a diagnostic or therapeutic agent attached to a flk-1bp polypeptide. The flk-1bp binds to the target cells, thus allowing detection thereof (in the case of diagnostic agents) or treatment thereof (with therapeutic agents).

Flk-1bp/diagnostic agent conjugates may be employed to detect the presence of flk-1$^+$ cells in vitro or in vivo. Conjugates containing a cytotoxic agent attached to flk-1bp may be used to kill flk-1$^+$ cells. In one embodiment, such conjugates containing cytotoxic agents are employed to kill flk-1$^+$ cells involved in angiogenesis.

Diagnostic and therapeutic agents that may be attached to a flk-1bp polypeptide include, but are not limited to, drugs, toxins, radionuclides, chromophores, enzymes that catalyze a colorimetric or fluorometric reaction, and the like, with the particular agent being chosen according to the intended application. Among the toxins are ricin, abrin, saporin toxin, diptheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the flk-1bp by any suitable conventional procedure. Being a protein, flk-1bp comprises functional groups on amino acid side chains that can be reacted with functional groups on a desired agent to form covalent bonds, for example. The agent may be covalently linked to flk-1bp via an amide bond, hindered disulfide bond, acid-cleavable linkage, and the like, which are among the conventional linkages chosen according to such factors as the structure of the desired agent. Alternatively, flk-1bp or the agent to be linked thereto may be derivatized to generate or attach a desired reactive functional group. The derivatization may involve attachment of one of the bifunctional coupling reagents available for linking various molecules to proteins (Pierce Chemical Company, Rockford, Ill.). A number of techniques for radiolabeling proteins are known. One such method involves use of commercially available reagents (Pierce Chemical Company) to radioiodinate a flk-1bp polypeptide. Radionuclide metals may be attached to flk-1bp by using a suitable bifunctional chelating agent, examples of which are described in U.S. Pat. Nos. 4,897,255 and 4,965,392.

Conjugates comprising flk-1bp and a suitable diagnostic or therapeutic agent (preferably covalently linked) are thus prepared. The conjugates are administered or otherwise employed in an amount appropriate for the particular indication.

The present invention provides pharmaceutical compositions comprising purified flk-1bp and a physiologically acceptable carrier, diluent, or excipient. Such compositions may comprise flk-1bp in any form described herein, e.g., full length native flk-1bp, or fragments, variants, oligomers, derivatives, or conjugates thereof. Components that are commonly employed in pharmaceutical formulations include those described in *Remington's Pharmaceutical Sciences and U.S. Pharmacopoeia: National Formulary*, Mack Publishing Company, Easton, Pa., 1984. Suitable carriers, diluents, and excipients are nontoxic to recipients at the dosages and concentrations employed. Such compositions may comprise buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients commonly employed in pharmaceutical compositions. Neutral buffered saline or saline mixed with conspecific serum albumin are among the appropriate diluents. The composition may be formulated as a lyophilizate using appropriate excipient solutions (e.g. sucrose) as diluents.

For therapeutic use, purified proteins of the present invention are administered to a patient, preferably a human, for treatment in a manner appropriate to the indication. Thus, for example, the pharmaceutical compositions can be administered locally, by intravenous injection, continuous infusion, sustained release from implants, or other suitable technique. Appropriate dosages and the frequency of administration will depend, of course, on such factors as the nature and severity of the indication being treated, the desired response, the condition of the patient and so forth.

The flk-1bp protein employed in the pharmaceutical compositions preferably is purified such that the flk-1bp protein is substantially free of other proteins of natural or endogenous origin, desirably containing less than about 1% by mass of protein contaminants residual of production processes. Such compositions, however, can contain other proteins added as stabilizers, carriers, excipients or co-therapeutics.

The flk-1bp of the present invention also finds use in various in vitro assays. In one such assay, a molecule is tested for the ability to compete with flk-1bp for binding to a given receptor. Other assays identify molecules that modulate angiogenesis. Such molecules may be proteins or small peptides, or may be non-proteinaceous in nature, and include naturally occurring or synthetic molecules.

Flk-1bp may be employed in screening assays to identify antagonists, i.e., molecules capable of inhibiting a biological activity of flk-1bp. In one embodiment, the assay identifies molecules that inhibit flk-1bp-mediated angiogenesis.

One method for identifying antagonists of flk-1bp comprises contacting cells expressing a receptor that binds flk-1bp with flk-1bp in the presence of a candidate antagonist, and analyzing whether the candidate antagonist inhibits a biological effect induced by the binding of flk-1bp to the cells. One of the above-described diagnostic (detectable) agents may be attached to the flk-1bp. In one embodiment, the receptor is flk-1. Suitable cells include, but are not limited to, flk-1$^+$ endothelial cells, e.g., flk-1$^+$ vascular endothelial cells. In particular embodiments, the biological effect is proliferation of the cells or phosphorylation of the receptor.

Inhibitors (antagonists) of flk-1bp that are identified in such screening assays are provided, along with compositions containing the inhibitors. The thus-identified antagonists may be employed to inhibit a biological activity of flk-1bp, e.g., may be administered in vivo to treat conditions mediated (directly or indirectly) by flk-1bp. The antagonists find use in inhibiting angiogenesis, including the angiogenesis associated with growth of solid tumors.

The flk-1bp-encoding DNAs disclosed herein find use in the production of flk-1bp polypeptides, as discussed above. Fragments of the flk-1bp nucleotide sequences are also useful. In one embodiment, such fragments comprise at least about 17 consecutive nucleotides, more preferably at least 30 consecutive nucleotides, of the flk-1bp DNA disclosed herein. DNA and RNA complements of said fragments are provided herein, along with both single-stranded and double-stranded forms of the flk-1bp DNA of SEQ ID NO:1.

Among the uses of such flk-1bp nucleic acid fragments are use as a probe or as primers in a polymerase chain reaction (PCR). As one example, such a probe finds use in detecting the presence of flk-1bp nucleic acids in in vitro assays and in such procedures as Northern and Southern blots. Cell types expressing flk-1bp can be identified as well. Such procedures are well known, and the skilled artisan can choose a probe of suitable length, depending on the particular intended application. For PCR, 5' and 3' primers corresponding to the termini of a desired flk-1bp DNA are employed in isolating and amplifying the DNA, using conventional techniques.

Other useful fragments of flk-1bp nucleic acids are antisense or sense oligonucleotides comprising a single-stranded nucleic acid sequence (either RNA or DNA) capable of binding to target flk-1bp mRNA (sense) or flk-1bp DNA (antisense) sequences. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of flk-1bp proteins.

Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT Application US 90/02656). Alternatively, other promotor sequences may be used to express the oligonucleotide.

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antibodies Immunoreactive with flk-1bp

The flk-1bp protein of the present invention, or immunogenic fragments thereof, may be employed in generating antibodies. The present invention thus provides antibodies that specifically bind flk-1bp, i.e., the antibodies bind to flk-1bp via the antigen-binding sites of the antibody (as opposed to non-specific binding).

Polyclonal and monoclonal antibodies directed against flk-1bp may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988). Production of monoclonal antibodies that are immunoreactive with flk-1bp is further illustrated in example 3 below.

Antigen-binding fragments of such antibodies, which may be produced by conventional techniques, are also encompassed by the present invention. Examples of such fragments include, but are not limited to, Fab, F(ab'), and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993).

Among the uses of the antibodies is use in assays to detect the presence of flk-1bp polypeptides, either in vitro or in vivo. The antibodies find further use in purifying flk-1bp by affinity chromatography.

Certain of the antibodies may additionally be able to block binding of flk-1bp to target cells and to inhibit a biological activity of flk-1bp in vivo. A therapeutic method involves in vivo administration of such an antibody in an amount effective in inhibiting an flk-1bp-mediated biological activity. Disorders mediated or exacerbated by flk-1bp, directly or indirectly, are thus treated. In one embodiment, such an antibody is administered to a mammal to inhibit angiogenesis.

Pharmaceutical compositions comprising an antibody that specifically binds flk-1bp, and a suitable, diluent, excipient, or carrier, are provided herein. Suitable components of such compositions are as described above for the compositions containing flk-1bp proteins.

The following examples are provided to illustrate particular embodiments of the present invention, and are not to be construed as limiting the scope of the invention.

EXAMPLE 1

Isolation of a Human flk-1bp DNA

DNA encoding a human flk-1bp protein was isolated by the following procedure. A search of a sequence databank was performed, using a vascular endothelial cell growth factor (VEGF) amino acid sequence as the query sequence. An expressed sequence tag (EST) file, GenBank accession number Z44272, was identified by the search.

Two oligonucleotides based upon sequences at the 3' and 5' ends of this 299-nucleotide EST file were synthesized for use as polymerase chain reaction (PCR) primers. PCR was conducted by conventional procedures, using DNA from a WI-26VA4 (human fibroblast cell line; see below) cDNA library in a λgt10 vector as the template. A 299-bp DNA fragment that was isolated and amplified by the PCR corresponded to nucleotides 660 to 958 of SEQ ID NO:1.

A cDNA library derived from a human fibroblast cell line designated WI-26VA4 was prepared by isolating polyA$^+$ RNA from WI-26VA4 cells cultured in the presence of pokeweed mitogen. cDNA was synthesized on the mRNA template by conventional techniques. Double stranded cDNA at least about 500 bp in length was inserted into an expression vector designated pDC302. The mammalian expression vector pDC302, which also replicates in E. coli, is described in Mosley et al. (Cell 59:335–348, 1989).

The 299-bp DNA fragment isolated above was labeled with $^{32}$P and used as a probe to screen the human fibroblast cDNA library. The nucleotide sequence of a positive clone, designated human flk-1bp clone 9C1, was determined, and is presented in SEQ ID NO:1. The amino acid sequence encoded thereby is presented in SEQ ID NO:2. This human flk-1bp is a secreted (as opposed to cell membrane bound) protein comprising an N-terminal signal peptide (amino acids −20 to −1 of SEQ ID NO:2) followed by the mature protein (amino acids 1 to 399). The calculated molecular weight of the mature form of this protein is 44,823 daltons, and the predicted pI is 8.678.

E. coli strain DH10B cells transformed with a recombinant vector containing this flk-1bp DNA were deposited with the American Type Culture Collection on Sep. 1, 1995, and assigned accession no. ATCC 69897. The deposit was made under the terms of the Budapest Treaty. The vector in the deposited strain is the cloning vector pBluescript®SK(−) (Stratagene Cloning Systems, LaJolla, Calif.). The vector was digested with EcoRI (found in the multiple cloning site of the vector), and human flk-1bp DNA that includes the entire coding region shown in SEQ ID NO:1, as well as additional 5' and 3' non-coding sequences, was ligated into the digested vector.

EXAMPLE 2

Competition Binding Assay

Human flk-1bp was expressed and tested for the ability to compete with VEGF for binding the receptor designated flk-1, as follows. A cDNA encoding amino acids −20 to 399 of SEQ ID NO:2 was inserted into the expression vector pDC302 (Mosley et al., Cell 59:335–348, 1989). CV-1/EBNA-1 cells were transfected with the resulting recombinant expression vector. The monkey kidney cell line CV-1/EBNA-1 (ATCC CRL 10478) was derived by transfection of the CV-1 cell line (ATCC CCL 70) with a gene encoding Epstein-Barr virus nuclear antigen-1 (EBNA-1) that constitutively expresses EBNA-1 driven from the human CMV intermediate-early enhancer/promoter, as described by McMahan et al. (EMBO J. 10:2821, 1991).

The transfected cells were cultured to allow secretion of the flk-1bp into the culture medium. Cells were pelleted by centrifugation, and culture supernatants were concentrated 10-fold for use in the following assay.

Human vascular endothelial cell growth factor (VEGF), which is known to bind flk-1, was radioiodinated using standard techniques. The ability of the flk-1bp-containing supernatant to compete with the radioiodinated VEGF for binding to a human flk-1/Fc fusion protein was tested. The fusion protein comprised the extracellular domain of human flk-1 fused to an Fc region polypeptide derived from an antibody. Flk-1/Fc fusion proteins may be prepared by procedures analogous to those described in Park et al. (J. Biol. Chem. 269:25646, 1994, at page 25647), hereby incorporated by reference.

The flk-1bp-containing supernatant inhibited about 80% of the binding of VEGF to the flk-1/Fc fusion protein. Control supernatant from CV1-EBNA cells inhibited about 20% of the VEGF binding to flk-1/Fc.

EXAMPLE 3

Antibodies that Bind flk-1bp

This example illustrates the preparation of monoclonal antibodies that specifically bind flk-1bp. Suitable immunogens that may be employed in generating such antibodies include, but are not limited to, purified flk-1bp protein, an immunogenic fragment thereof, and fusion proteins containing flk-1bp polypeptides (e.g., flk-1bp/Fc fusion proteins).

Known techniques for producing monoclonal antibodies include those described in U.S. Pat. No. 4,411,993. Briefly, mice are immunized with flk-1bp as an immunogen emulsified in complete Freund's adjuvant, and injected in amounts ranging from 10–100 μg subcutaneously or intraperitoneally. Ten to twelve days later, the immunized animals are boosted with additional flk-1bp emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immuno-sorbent Assay) for antibodies directed against flk-1bp.

Following detection of an appropriate antibody titer, positive animals are provided one last intravenous injection of flk-1bp in saline. Three to four days later, the animals are sacrificed, spleen cells harvested, and spleen cells are fused to a murine myeloma cell line such as NS1 or, preferably, P3x63Ag 8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified flk-1bp by adaptations of the techniques disclosed in Engvall et al. (Immunochem. 8:871, 1971) and in U.S. Pat. No. 4,703,004. Positive hybridoma cells can be injected intraperitoneally into syngeneic BALB/c mice to produce ascites containing high concentrations of anti-flk-1bp monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can be used, as can affinity chromatography based upon binding to flk-1bp.

EXAMPLE 4

Northern Blot Analysis

Expression of flk-1bp in a number of different tissue types was analysed in a conventional northern blot procedure. Northern blots containing poly A$^+$ RNA from a variety of adult human tissues was obtained from Clonetech (Palo Alto, Calif.). The blots were probed with an antisense riboprobe derived from human flk-1bp DNA.

Human flk-1bp mRNA was detected in heart, liver, skeletal muscle, pancreas, and prostate, with weaker but detectable expression in brain, placenta, lung, kidney, spleen, thymus, colon, ovaries, and small intestine. Human flk-1bp message was not detected in peripheral blood leukocytes.

What is claimed is:

1. An isolated nucleic acid molecule encoding a flk-1 binding protein (flk-1bp), when said flk-1bp comprises an amino acid sequence selected from the group consisting of residues −20 to 399 of SEQ ID NO:2 and residues 1 to 399 of SEQ ID NO:2.

2. An expression vector comprising the nucleic acid molecule of claim 1.

3. A process for preparing a flk-1bp polypeptide, comprising culturing a host cell transformed with a vector of claim 2 under conditions promoting expression of flk-1bp and recovering the flk-1bp polypeptide.

4. An isolated nucleic acid molecule comprising a nucleotide sequence selected from the group consisting of nucleotides 188 to 1444 of SEQ ID NO:1 and nucleotides 248 to 1444 of SEQ ID NO:1.

5. An expression vector comprising the nucleic acid molecule of claim 4.

6. A process for preparing a flk-1bp polypeptide, comprising culturing a host cell transformed with a vector of claim 5 under conditions promoting expression of flk-1bp and recovering the flk-1 bp polypeptide.

7. An isolated nucleic acid molecule encoding a flk-1bp polypeptide, when said nucleic acid molecule comprises the flk-1bp cDNA insert of the vector deposited in strain ATCC 69897.

8. An expression vector comprising the nucleic acid molecule of claim 7.

9. A process for preparing a flk-1bp polypeptide, comprising culturing a host cell transformed with a vector of claim 8 under conditions promoting expression of flk-1bp and recovering the flk-1 bp polypeptide.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2321 base pairs
      (B) TYPE: nucleic acid
      (C) STRANDEDNESS: single
      (D) TOPOLOGY: linear (iii) HYPOTHETICAL: NO (iv) ANTI-SENSE: NO (vii) IMMEDIATE SOURCE:
      (B) CLONE: hu flk-1 bp (ix) FEATURE:
      (A) NAME/KEY: CDS
      (B) LOCATION: 188..1447

(ix) FEATURE:
      (A) NAME/KEY: sig_peptide
      (B) LOCATION: 188..247

(ix) FEATURE:
      (A) NAME/KEY: mat_peptide
      (B) LOCATION: 248..1444

(xi) SEQUENCE DESCRIPTION: SEQ ID NO:1:

```
GAATTCGCGG CCGCTGGGAA CGCGGAGCCC CGGACCCGCT CCCGCCGCCT CCGACTCGCC    60

CAGGGGGGGT CGCCGGGAGG AGCCCGGGGG AGAGGGACCA GGAGGGGCCC GCGGCCTCGC   120

AGGGGCGCCC GCGCCCCCAC CCCTGCCCCC GCCAGCGGAC CGGTCCCCCA CCCCCGGTCC   180

TTCCACC ATG CAC TTG CTG GGC TTC TTC TCT GTG GCG TGT TCT CTG CTC    229
        Met His Leu Leu Gly Phe Phe Ser Val Ala Cys Ser Leu Leu
            -20             -15                 -10

GCC GCT GCG CTG CTC CCG GGT CCT CGC GAG GCG CCC GCC GCC GCC GCC    277
Ala Ala Ala Leu Leu Pro Gly Pro Arg Glu Ala Pro Ala Ala Ala Ala
    -5               1               5                   10

GCC TTC GAG TCC GGA CTC GAC CTC TCG GAC GCG GAG CCC GAC GCG GGC    325
Ala Phe Glu Ser Gly Leu Asp Leu Ser Asp Ala Glu Pro Asp Ala Gly
                15                  20                  25

GAG GCC ACG GCT TAT GCA AGC AAA GAT CTG GAG GAG CAG TTA CGG TCT    373
Glu Ala Thr Ala Tyr Ala Ser Lys Asp Leu Glu Glu Gln Leu Arg Ser
                30                  35                  40

GTG TCC AGT GTA GAT GAA CTC ATG ACT GTA CTC TAC CCA GAA TAT TGG    421
Val Ser Ser Val Asp Glu Leu Met Thr Val Leu Tyr Pro Glu Tyr Trp
            45                  50                  55

AAA ATG TAC AAG TGT CAG CTA AGG AAA GGA GGC TGG CAA CAT AAC AGA    469
Lys Met Tyr Lys Cys Gln Leu Arg Lys Gly Gly Trp Gln His Asn Arg
        60                  65                  70

GAA CAG GCC AAC CTC AAC TCA AGG ACA GAA GAG ACT ATA AAA TTT GCT    517
Glu Gln Ala Asn Leu Asn Ser Arg Thr Glu Glu Thr Ile Lys Phe Ala
75                  80                  85                  90

GCA GCA CAT TAT AAT ACA GAG ATC TTG AAA AGT ATT GAT AAT GAG TGG    565
Ala Ala His Tyr Asn Thr Glu Ile Leu Lys Ser Ile Asp Asn Glu Trp
                95                  100                 105

AGA AAG ACT CAA TGC ATG CCA CGG GAG GTG TGT ATA GAT GTG GGG AAG    613
Arg Lys Thr Gln Cys Met Pro Arg Glu Val Cys Ile Asp Val Gly Lys
            110                 115                 120
```

```
GAG TTT GGA GTC GCG ACA AAC ACC TTC TTT AAA CCT CCA TGT GTG TCC      661
Glu Phe Gly Val Ala Thr Asn Thr Phe Phe Lys Pro Pro Cys Val Ser
        125                 130                 135

GTC TAC AGA TGT GGG GGT TGC TGC AAT AGT GAG GGG CTG CAG TGC ATG      709
Val Tyr Arg Cys Gly Gly Cys Cys Asn Ser Glu Gly Leu Gln Cys Met
        140                 145                 150

AAC ACC AGC ACG AGC TAC CTC AGC AAG ACG TTA TTT GAA ATT ACA GTG      757
Asn Thr Ser Thr Ser Tyr Leu Ser Lys Thr Leu Phe Glu Ile Thr Val
155                 160                 165                 170

CCT CTC TCT CAA GGC CCC AAA CCA GTA ACA ATC AGT TTT GCC AAT CAC      805
Pro Leu Ser Gln Gly Pro Lys Pro Val Thr Ile Ser Phe Ala Asn His
                175                 180                 185

ACT TCC TGC CGA TGC ATG TCT AAA CTG GAT GTT TAC AGA CAA GTT CAT      853
Thr Ser Cys Arg Cys Met Ser Lys Leu Asp Val Tyr Arg Gln Val His
            190                 195                 200

TCC ATT ATT AGA CGT TCC CTG CCA GCA ACA CTA CCA CAG TGT CAG GCA      901
Ser Ile Ile Arg Arg Ser Leu Pro Ala Thr Leu Pro Gln Cys Gln Ala
                205                 210                 215

GCG AAC AAG ACC TGC CCC ACC AAT TAC ATG TGG AAT AAT CAC ATC TGC      949
Ala Asn Lys Thr Cys Pro Thr Asn Tyr Met Trp Asn Asn His Ile Cys
220                 225                 230

AGA TGC CTG GCT CAG GAA GAT TTT ATG TTT TCC TCG GAT GCT GGA GAT      997
Arg Cys Leu Ala Gln Glu Asp Phe Met Phe Ser Ser Asp Ala Gly Asp
235                 240                 245                 250

GAC TCA ACA GAT GGA TTC CAT GAC ATC TGT GGA CCA AAC AAG GAG CTG     1045
Asp Ser Thr Asp Gly Phe His Asp Ile Cys Gly Pro Asn Lys Glu Leu
                255                 260                 265

GAT GAA GAG ACC TGT CAG TGT GTC TGC AGA GCG GGG CTT CGG CCT GCC     1093
Asp Glu Glu Thr Cys Gln Cys Val Cys Arg Ala Gly Leu Arg Pro Ala
            270                 275                 280

AGC TGT GGA CCC CAC AAA GAA CTA GAC AGA AAC TCA TGC CAG TGT GTC     1141
Ser Cys Gly Pro His Lys Glu Leu Asp Arg Asn Ser Cys Gln Cys Val
                285                 290                 295

TGT AAA AAC AAA CTC TTC CCC AGC CAA TGT GGG GCC AAC CGA GAA TTT     1189
Cys Lys Asn Lys Leu Phe Pro Ser Gln Cys Gly Ala Asn Arg Glu Phe
300                 305                 310

GAT GAA AAC ACA TGC CAG TGT GTA TGT AAA AGA ACC TGC CCC AGA AAT     1237
Asp Glu Asn Thr Cys Gln Cys Val Cys Lys Arg Thr Cys Pro Arg Asn
315                 320                 325                 330

CAA CCC CTA AAT CCT GGA AAA TGT GCC TGT GAA TGT ACA GAA AGT CCA     1285
Gln Pro Leu Asn Pro Gly Lys Cys Ala Cys Glu Cys Thr Glu Ser Pro
                335                 340                 345

CAG AAA TGC TTG TTA AAA GGA AAG AAG TTC CAC CAC CAA ACA TGC AGC     1333
Gln Lys Cys Leu Leu Lys Gly Lys Lys Phe His His Gln Thr Cys Ser
            350                 355                 360

TGT TAC AGA CGG CCA TGT ACG AAC CGC CAG AAG GCT TGT GAG CCA GGA     1381
Cys Tyr Arg Arg Pro Cys Thr Asn Arg Gln Lys Ala Cys Glu Pro Gly
                365                 370                 375

TTT TCA TAT AGT GAA GAA GTG TGT CGT TGT GTC CCT TCA TAT TGG AAA     1429
Phe Ser Tyr Ser Glu Glu Val Cys Arg Cys Val Pro Ser Tyr Trp Lys
380                 385                 390

AGA CCA CAA ATG AGC TAA GATTGTACTG TTTTCCAGTT CATCGATTTT            1477
Arg Pro Gln Met Ser *
395                 400

CTATTATGGA AAACTGTGTT GCCACAGTAG AACTGTCTGT GAACAGAGAG ACCCTTGTGG   1537

TCCATGCTAA CAAAGACAAA AGTCTGTCTT TCCTGAACCA TGTGGATAAC TTTACAGGAA   1597

ATGGTACTGG AGCTCATCTG CAAAAGGCCT CTTGTGAAGA CTGGTTTTCT GCCAATGACC   1657

AAACAGCCAA GATTTCCTCT CGTGATTTCT TTAAAAGAAT GACTATATAA TTTATTTCCA   1717
```

-continued

```
CTAAAAATAT TGTTTCTGCA TTCATTTTTA TAGCAACAAC AATTGGTAAA ACTCACTGTG    1777

ATCAATATTT TTATATCATG CAAAATATGT TTAAAATAAA ATGAAAATTG TATTATAAGC    1837

TGCTAAGTTC AGTCCATTAT CATCTTACAT GATGAACGAA AACTACTATC ATGAAGACAC    1897

TGATCTTTCT CTGCCCTTTT TTGTTCTCTA ACCAGATGTC ACATATGTAT TACTATGATA    1957

AAAAGTATGA TCCTGTGAAA GAGAGTGTCA GAGGACAACA GAATGCTATT GCTTCATCTC    2017

TTATATGTTT AATGATTATA AACATTTTAG TACATGATAC TTTTGAATTT ATGACCAAGT    2077

GAATCAATAT GAAACATCTT GTAAGATAGA CTACTTAGCA TTGTGATTAA AAGTCATTCA    2137

GTGCTCTGAG AACATTCAGA ATCTTACGTT GGTAGAAAAT CCTGCAGTAT ATATTAAAAT    2197

GGCTTTAAAT ATTTTCTCAA AAATAATCTT TTCCAAATAT TTGACTTTTT CTGGCCAGCT    2257

AAAATACTTT TTGTGAGTGG AAGTGCTCCT ATCCAAACAT TTTAAAAAAA GCGCCCGCGA    2317

ATTC                                                                 2321
```

(2) INFORMATION FOR SEQ ID NO:2:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Leu Leu Gly Phe Phe Ser Val Ala Cys Ser Leu Leu Ala Ala
-20             -15                 -10                 -5

Ala Leu Leu Pro Gly Pro Arg Glu Ala Pro Ala Ala Ala Ala Phe
                 1               5                  10

Glu Ser Gly Leu Asp Leu Ser Asp Ala Glu Pro Asp Ala Gly Glu Ala
            15                  20                  25

Thr Ala Tyr Ala Ser Lys Asp Leu Glu Glu Gln Leu Arg Ser Val Ser
        30                  35                  40

Ser Val Asp Glu Leu Met Thr Val Leu Tyr Pro Glu Tyr Trp Lys Met
45                  50                  55                  60

Tyr Lys Cys Gln Leu Arg Lys Gly Gly Trp Gln His Asn Arg Glu Gln
                65                  70                  75

Ala Asn Leu Asn Ser Arg Thr Glu Glu Thr Ile Lys Phe Ala Ala Ala
            80                  85                  90

His Tyr Asn Thr Glu Ile Leu Lys Ser Ile Asp Asn Glu Trp Arg Lys
        95                  100                 105

Thr Gln Cys Met Pro Arg Glu Val Cys Ile Asp Val Gly Lys Glu Phe
    110                 115                 120

Gly Val Ala Thr Asn Thr Phe Phe Lys Pro Pro Cys Val Ser Val Tyr
125                 130                 135                 140

Arg Cys Gly Gly Cys Cys Asn Ser Glu Gly Leu Gln Cys Met Asn Thr
                145                 150                 155

Ser Thr Ser Tyr Leu Ser Lys Thr Leu Phe Glu Ile Thr Val Pro Leu
            160                 165                 170

Ser Gln Gly Pro Lys Pro Val Thr Ile Ser Phe Ala Asn His Thr Ser
        175                 180                 185

Cys Arg Cys Met Ser Lys Leu Asp Val Tyr Arg Gln Val His Ser Ile
    190                 195                 200

Ile Arg Arg Ser Leu Pro Ala Thr Leu Pro Gln Cys Gln Ala Ala Asn
205                 210                 215                 220
```

```
Lys Thr Cys Pro Thr Asn Tyr Met Trp Asn Asn His Ile Cys Arg Cys
                225                 230                 235

Leu Ala Gln Glu Asp Phe Met Phe Ser Ser Asp Ala Gly Asp Asp Ser
                240                 245                 250

Thr Asp Gly Phe His Asp Ile Cys Gly Pro Asn Lys Glu Leu Asp Glu
                255                 260                 265

Glu Thr Cys Gln Cys Val Cys Arg Ala Gly Leu Arg Pro Ala Ser Cys
                270                 275                 280

Gly Pro His Lys Glu Leu Asp Arg Asn Ser Gln Cys Val Cys Lys
285                 290                 295                 300

Asn Lys Leu Phe Pro Ser Gln Cys Gly Ala Asn Arg Glu Phe Asp Glu
                305                 310                 315

Asn Thr Cys Gln Cys Val Cys Lys Arg Thr Cys Pro Arg Asn Gln Pro
                320                 325                 330

Leu Asn Pro Gly Lys Cys Ala Cys Glu Cys Thr Glu Ser Pro Gln Lys
                335                 340                 345

Cys Leu Leu Lys Gly Lys Lys Phe His His Gln Thr Cys Ser Cys Tyr
                350                 355                 360

Arg Arg Pro Cys Thr Asn Arg Gln Lys Ala Cys Glu Pro Gly Phe Ser
365                 370                 375                 380

Tyr Ser Glu Glu Val Cys Arg Cys Val Pro Ser Tyr Trp Lys Arg Pro
                385                 390                 395

Gln Met Ser (2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
         (B) CLONE: FLAG peptide (xi) SEQUENCE DESCRIPTION: SEQ ID NO:3:

Asp Tyr Lys Asp Asp Asp Asp Lys
1               5

(2) INFORMATION FOR SEQ ID NO:4:

(i) SEQUENCE CHARACTERISTICS:
        (A) LENGTH: 191 amino acids
        (B) TYPE: amino acid
        (D) TOPOLOGY: linear (ii) MOLECULE TYPE: protein (iii) HYPOTHETICAL: NO (vii) IMMEDIATE SOURCE:
         (B) CLONE: Hu VEGF (xi) SEQUENCE DESCRIPTION: SEQ ID NO:4:

Met Asn Phe Leu Leu Ser Trp Val His Trp Ser Leu Ala Leu Leu Leu
1               5                   10                  15
```

-continued

```
Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Gly Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

(2) INFORMATION FOR SEQ ID NO:5:

(i) SEQUENCE CHARACTERISTICS:
        (A) LENGTH: 149 amino acids
        (B) TYPE: amino acid
        (D) TOPOLOGY: linear (ii) MOLECULE TYPE: protein (iii) HYPOTHETICAL: NO (vii) IMMEDIATE SOURCE:
        (B) CLONE: Hu PLGF (xi) SEQUENCE DESCRIPTION: SEQ ID NO:5:

Met Pro Val Met Arg Leu Phe Pro Cys Phe Leu Gln Leu Leu Ala Gly
 1               5                  10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
            35                  40                  45

Arg Ser Tyr Cys Arg Ala Leu Glu Arg Leu Val Asp Val Val Ser Glu
 50                  55                  60

Tyr Pro Ser Glu Val Glu His Met Phe Ser Pro Ser Cys Val Ser Leu
 65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
            115                 120                 125
```

-continued

```
Glu Cys Arg Pro Leu Arg Glu Lys Met Lys Pro Glu Arg Cys Gly Asp
    130                 135                 140

Ala Val Pro Arg Arg
145
```